United States Patent [19]

Rounbehler

[11] Patent Number: 4,775,633

[45] Date of Patent: Oct. 4, 1988

[54] DETECTION OF HYDRAZINE COMPOUNDS IN GASEOUS SAMPLES BY THEIR CONVERSION TO NITRIC OXIDE-YIELDING DERIVATIVES

[75] Inventor: David P. Rounbehler, Plymouth, Mass.

[73] Assignee: Thermedics Inc., Woburn, Mass.

[21] Appl. No.: 4,237

[22] Filed: Jan. 5, 1987

Related U.S. Application Data

[63] Continuation of Ser. No. 604,260, Apr. 26, 1984, abandoned, which is a continuation-in-part of Ser. No. 410,280, Aug. 23, 1982, abandoned.

[51] Int. Cl.$^4$ .................. G01N 21/76; G01N 31/12
[52] U.S. Cl. .................. 436/106; 422/238; 436/111; 436/128; 436/155; 436/158; 436/159; 436/160
[58] Field of Search .............. 436/106, 111, 114, 116, 436/117, 118, 128, 135, 155, 159, 160, 172, 158; 422/238

[56] References Cited

U.S. PATENT DOCUMENTS

| | | | |
|---|---|---|---|
| 1,292,715 | 1/1919 | Cox | 422/238 X |
| 2,883,423 | 4/1959 | Mosher et al. | 436/128 X |
| 3,287,089 | 11/1966 | Wilburn | 23/254 |
| 3,877,875 | 4/1975 | Jones et al. | 23/230 PC |
| 3,904,371 | 9/1975 | Neti et al. | 23/232 R |
| 3,967,933 | 7/1976 | Etess et al. | 436/116 X |
| 3,973,910 | 8/1976 | Fine | 23/230 PC |
| 3,996,002 | 12/1976 | Fine | 23/230 PC |
| 4,018,562 | 4/1977 | Parks et al. | 23/230 PC |
| 4,070,155 | 1/1978 | Fraim | 23/230 PC |
| 4,200,608 | 4/1980 | Croomes et al. | 422/97 |
| 4,301,114 | 11/1981 | Rounbehler et al. | 422/52 |
| 4,309,262 | 1/1982 | Levine et al. | 204/195 R |
| 4,395,494 | 7/1983 | Bodart et al. | 436/111 |

OTHER PUBLICATIONS

Volltrauer et al., "Breadboard Chemiluminescent Analyzer for Measurement of Hydrazines", Aerochem Final Report to Air Force, Report Number SAM-TR-77-36, Dec. 1977.

Saunders et al., "Detection and Monitoring of Hydrazine, Monomethylhydrazine, and their Decomposition Products", Naval Research Lab Memorandum Report 3313, Jun. 1976.

Mazur et al., Am. Ind. Hyg. Assoc. J., vol. 41, pp. 66-69, Jan. 1980.

Overberger et al., Organic Compounds With Nitrogen-Nitrogen Bonds, The Ronald Press Company, New York 1966, Secs. 1-2,1-3,2-1,2-2,2-3,3-1.

Tuazon et al., American Chemical Society, vol. 15, No. 7, pp. 823-828, Jul. 1981.

Veal, J. T., "The Analysis of Hydrazine, Monomethyl Hydrazine And 1,1-Dimethyl Hydrazine Using WCOT/GC Techniques", *Proc. Conf. Environ. Chem. Hydrazine Fuels*, 1977, pp. 79-97.

*Primary Examiner*—Barry S. Richman
*Assistant Examiner*—Robert J. Hill, Jr.
*Attorney, Agent, or Firm*—Herbert E. Messenger

[57] ABSTRACT

Disclosed is a method and apparatus for detecting hydrazine, monomethylhydrazine (MMH), and unsymmetrical dimethylhydrazine (UDMH) in a gaseous sample. The hydrazine compound detector includes a sample converter wherein vapors of an aldehyde such as acetaldehyde or a ketone such as acetone are mixed with a sample in gaseous form, and the mixture is allowed to react to form azine and hydrazone derivatives of the aldehyde or ketone. The derivatives may be transported long distances and then analyzed, as by heating in the presence of an oxidant in a pyrolyzer containing a nickel surface to produce nitric oxide (NO), followed by measurement of the NO in a NO detector such as a chemiluminescent analyzer.

10 Claims, 5 Drawing Sheets

DETECTION OF HYDRAZINE COMPOUNDS IN GASEOUS SAMPLES BY THEIR CONVERSION TO NITRIC OXIDE-YIELDING DERIVATIVES

CROSS REFERENCE TO RELATED APPLICATION

This application is a continuation of application Ser. No. 604,260, filed Apr. 26, 1984, and now abandoned, which in turn is a continuation-in-part of application Ser. No. 410,280, filed Aug. 23, 1982, and now abandoned.

BACKGROUND OF THE INVENTION

This invention relates to the detection of hydrazine compounds and particularly to the detection of hydrazine, monomethylhydrazine (MMH) and unsymmetrical dimethylhydrazine (UDMH) in gaseous samples using a technique whereby these compounds are converted to hydrazine derivatives which may readily be analyzed, as by oxidation to produce detectable nitric oxide (NO) gas.

Hydrazine compounds are used in a number of specialized commercial and military applications. Small amounts of hydrazine, for example, are often added to boiler water to retard corrosion, and hydrazine is also used as a fuel in rockets. Monomethylhydrazine (MMH) is employed as a propellant in space vehicle thrusters, and unsymmetrical dimethylhydrazine (UDMH) forms a major component of fuels for certain missiles. Since leakage or spillage of even small amounts of hydrazine compounds can yield harmful pollutants or lead to risk of explosion, it is often desirable to monitor samples, particularly air samples, for these compounds.

Various devices are known for detecting hydrazine compounds. Among these are infrared or photoacoustic spectrometers, electrochemical sensors containing electrolyte or ceramic beads which react when contacted by hydrazines, and colorimetric sensors. For example, U.S. Pat. No. 4,309,262 discloses a detector for hydrazine compounds which uses a ceramic pellet containing iridium to decompose fumes of the compounds and generate detectable heat.

Known hydrazine detectors, particularly those intended for detection of hydrazine compounds in gas samples, typically have one or more disadvantages which limit their utility. One common deficiency is a lack of selectivity due to interferences with other airborne compounds such as ammonia, oxygen, carbon dioxide, vehicular exhaust gases, and other organic compounds. Another drawback is a high level of maintenance required because of the need to replenish electrolyte, paper tape, or scrubbers or to make frequent corrections for drift. Many devices lack the sensitivity to detect hydrazines at the detection levels desired, and some (e.g., mass spectroscopy) are quite expensive and/or so complex as to require a highly skilled operator.

Other drawbacks of known hydrazine compound detectors are their inability to accurately perform analyses due to condensation or sticking of hydrazine compounds in sampling lines leading to the detector or in the detector itself.

Accordingly, it is an object of the invention to provide an improved method and apparatus for detecting hydrazine compounds.

It is a particular object of the invention to provide an improved apparatus for detecting hydrazine, monomethylhydrazine (MMH), and unsymmetrical dimethylhydrazine (UDMH) in gaseous samples.

It is an object of the invention to provide a method and apparatus for quantitative, continuous measurement of hydrazine compounds in gaseous samples.

It is an object of the invention to provide an improved method and apparatus for detecting hydrazine compounds in gaseous samples which permits low-loss sample transport along long lines, as from local sampling locations to a central analyzer.

It is also an object of the invention to provide a hydrazine compound detector which has high sensitivity, selectivity, and stability.

SUMMARY OF THE INVENTION

The invention concerns an improved method and apparatus for detection of hydrazine, monomethylhydrazine (MMH), and unsymmetrical dimethylhydrazine (UDMH), particularly in gaseous samples. These hydrazine compounds in a sample are converted to hydrazine derivatives by contacting the sample with an aldehyde or a ketone, then the derivatives are analyzed, as by prolyzing the derivatives to produce nitric oxide gas (NO) and measuring the nitric oxide gas. The invention provides continuous detection of gaseous hydrazine compounds at levels as low as a few parts per billion and essentially in real time—the departure from real time being essentially only the time needed for transport of the gaseous sample through a sample line to an analyzer.

The conversion of hydrazine compounds in a sample to hydrazine derivatives and the subsequent analysis of the derivatives may be performed in a single instrument or these functions may be accomplished in different parts of a detection system with remote sampling points and a centrally-located analyzer. In such a system the derivatives are formed near one or more sampling points and then transported along sample lines to an analyzer tied to a microprocessor-based computer.

A preferred hydrazine detector according to the invention includes a source of aldehyde or ketone vapors which continuously supplies the vapors to a sample line at a controlled rate to mix with a gaseous sample containing hydrazine compounds. A reaction chamber receives the gaseous mixture and provides a suitable surface and adequate reaction time of less than about ten seconds to permit conversion of hydrazine to an azine and conversion of MMH and UDMH to hydrazones. From the reaction chamber the hydrazones and azines are directed to a pyrolyzer where these hydrazine derivatives are heated in the presence of oxygen and a nickel surface to a temperature in the range of about 600° to 1000° C. The NO produced is then measured in an NO detector, preferably a detector which together with a processor/controller measures the radiation emitted during the chemiluminescent reaction of NO with ozone.

DETAILED DESCRIPTION OF PREFERRED EMBODIMENTS

Detection of hydrazine compounds according to the invention is based on conversion of hydrazine in gaseous samples to particular hydrazine derivatives which can readily be analyzed. One preferred method of analyzing the derivatives, which are preferably azines and hydrazones, is to heat them in the presence of an oxidant such as oxygen contained in air to form nitric oxide (NO), and then to measure the resulting NO.

In the invention as shown and described herein the term "hydrazine compound" refers to hydrazine, monomethylhydrazine (MMH), and unsymmetrical dimethylhydrazine (UDMH) which have the formulas:

In my work on analysis of nitrogen—containing organic compounds, I have determined that when unsymmetrical dimethylhydrazine (UDMH) is burned in air, half of the combined nitrogen in the UDMH is converted to nitric oxide (NO) whose detection (as by chemiluminescence) can be used to indicate the presence of UDMH. However, hydrazine and monomethylhydrazine (MMH) yield little or no chemiluminescence—detectable products when burned in air. Most likely the nitrogen in these latter compounds is instead converted to molecular nitrogen, which cannot readily be distinguished from molecular nitrogen in air present in the sample. Quite advantageously, however, I have discovered that if hydrazine, MMH and UDMH contained in a gas sample are first converted to certain hydrazine derivatives, the derivatives may then be readily detected. In particular the derivatives may be pyrolyzed to yield nitric oxide (NO), which is easily detectable by any of several techniques, such as the chemiluminescent reaction of NO with ozone, thereby permitting measurement of the hydrazine compounds in the sample.

In addition, I have found that the hydrazine derivatives, unlike the hydrazine compounds from which they are derived, are easily transported along sample lines and through various parts of instruments. Since the derivatives do not "stick" to sample lines and are stable during transport, the derivatization may be performed at locations remote from that at which the derivatives are analyzed.

Figure 1:
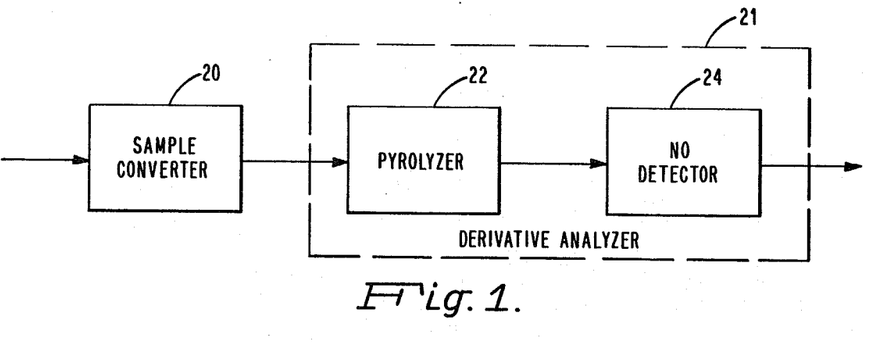
FIGS. 1 and 2 are block diagrams illustrating the elements of preferred hydrazine analyzers according to the invention.

The two basic elements of the apparatus for determining hydrazine compounds in a gaseous sample according to the invention are a sample converter 20 and a derivative analyzer 21 as shown in block diagram form in FIG. 1. Although the currently preferred derivative analyzer 21 includes a pyrolyzer 22 and a nitric oxide detector 24, which will be shown and described in considerable detail hereinafter, other analyzers may be appropriate—for example, the derivative analyzer 21 may comprise a spectro-photometric detector which passes an energy beam (in the infrared, ultraviolet, or other part of the spectrum) through a gas and then measures the energy emitted or absorbed by the gas.

According to the above-noted preferred embodiment, a gaseous sample to be tested for hydrazine compounds is first directed into the sample converter 20, for example, the sample may be drawn into the converter by action of a vacuum pump in the NO detector 24. The sample converter 20 operates on a sample by converting the hydrazine compounds therein to hydrazine derivatives in vaporous form, specifically to hydrazones and azines, which are then passed to the pyrolyzer 22. The pyrolyzer 22 heats the hydrazine derivatives in the sample, in the presence of an oxidant, to a temperature sufficient to convert essentially all of the nitrogen contained in the derivatives to nitric oxide gas (NO). The oxidant can, for example, be oxygen in air forming part of the sample. A preferred pyrolyzer temperature is in the range of 600°–1000° C.

The gaseous products of the pyrolyzer 22 are fed to an NO detector 24, which is preferably a chemiluminescent analyzer but may comprise any other instrument suitable for accurately measuring NO. For example, a non-dispersive infrared radiation instrument, an ion-generating detector or an analyzer employing the Saltzman wet chemistry method or other chemical technique may be used. The NO detector 24 produces a signal directly related to the amount of NO present in the pyrolyzer products and therefore directly related to the amount of hydrazine compounds present in the sample.

Figure 2:
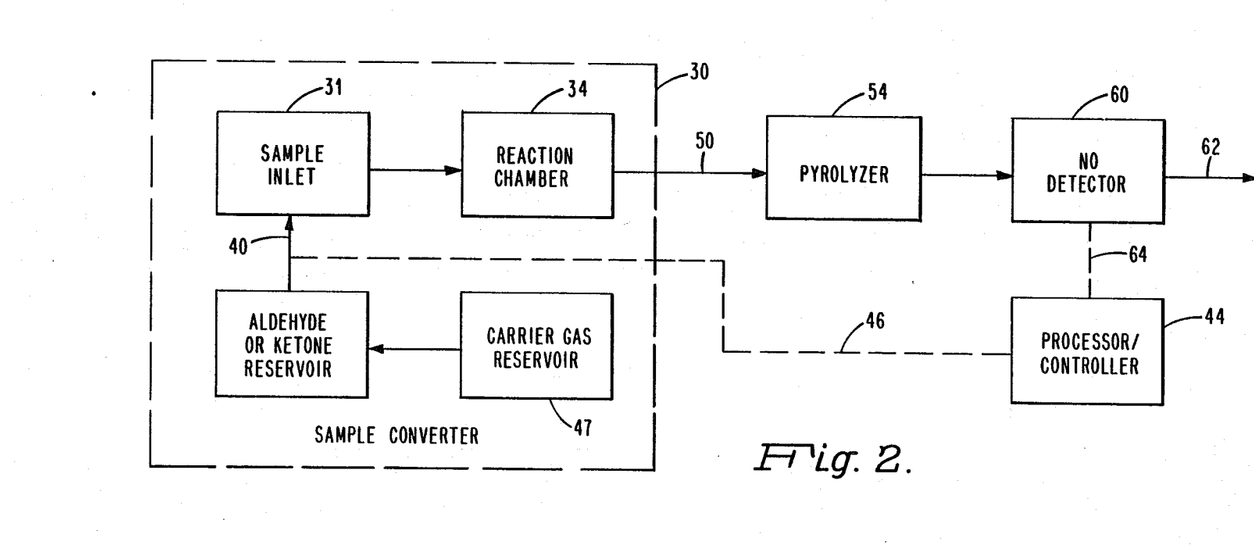
Figure 3:
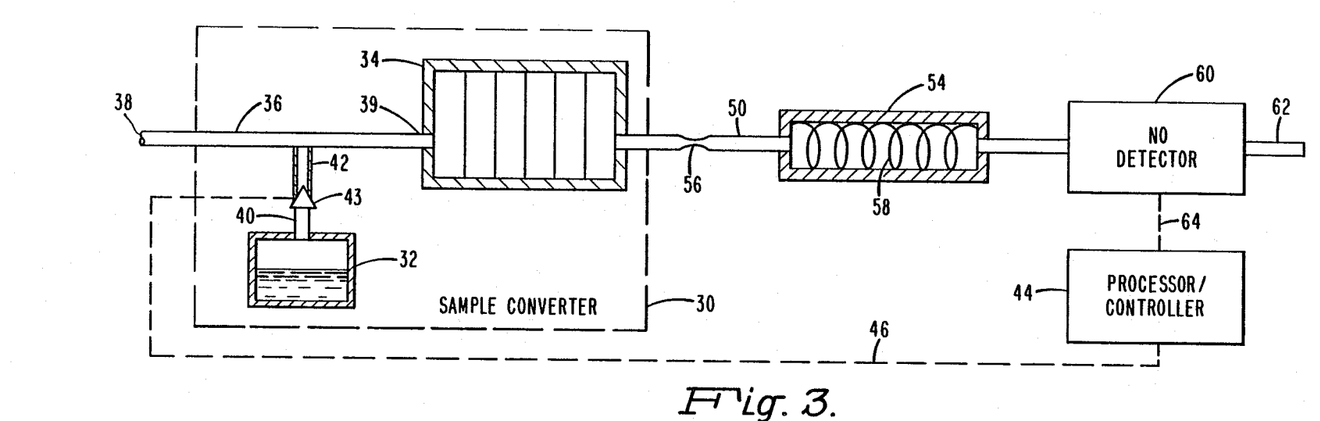
FIG. 3 is a diagram showing, partly in block diagram form and partly in cross-section, a hydrazine analyzer according to the invention.

FIGS. 2 and 3 illustrate preferred embodiments of the hydrazine compound analyzer of the invention, with FIG. 3 showing partial sectional views of certain components of the analyzer such as the converter 30. The converter 30 preferably comprises a sample inlet 31 for receiving a sample, an aldehyde or ketone reservoir 32 operable to supply aldehyde or ketone to the sample inlet 31, and a reaction chamber 34.

The sample inlet 31 typically comprises a sample line 36 (FIG. 3) having an inlet end 38 for receiving a gas sample and an outlet end 39 connected to the reaction chamber 34. A supply line 40 extends between the sample line 36 and the reservoir 32 to permit introduction of vapors from the reservoir 32 into the sample line 36 to mix with the gas sample ahead of the reaction chamber 34. Included in the sample converter 30 are means for controlling the rate of flow of vapors from the reservoir 32 into the sample line 36. For example, a diffusion tube 42 may be included in or constitute the supply line 40. The means for controlling flow may also comprise a valve 43 electrically connected to a processor/controller 44 by a line 46. Flow through the supply line 40 may also be established and controlled by supplying a carrier gas such as nitrogen to the reservoir 32 from a carrier gas reservoir 47 (FIG. 2) to sweep vapors from the reservoir 32 to the sample line 36. The flow preferably is regulated to supply an excess of aldehyde or ketone to line 36.

The reservoir 32 is any suitable source of vapors of an aldehyde or ketone or mixture thereof. As indicated above, the reservoir 32 may include or be connected to a source of an inlet carrier gas to promote and control flow of vapors therefrom. Also, depending on the boiling point of the aldehyde or ketone utilized, the reservoir 32 may include a heater (not shown) for controlling temperature of the aldehyde or ketone.

It is preferred that the gas sample contain air to assist in the conversion of the hydrazine compounds to hydrazine derivatives in the reaction chamber 34 and to provide oxygen required in subsequent pyrolysis of the derivatives. Accordingly, if the sample is known to not include air, as when standard samples of hydrazine compounds are prepared for testing using an inert carrier gas and a hydrazine compound in liquid form, air may be fed to the sample line 36 by means of an air line (not shown) at a position intermediate between the inlet end 38 and the outlet end 39 of the sample line 36. One benefit of air in the reaction chamber is that it converts a small part of the acetaldehyde or acetone vapor to acetic acid which thereafter catalyzes the derivatization of the hydrazine compounds—i.e., increases the rate of reaction of the aldehyde or ketone with the hydrazine compounds.

Among the aldehydes which can be utilized in the reservoir 32, acetaldehyde ($HCOCH_3$) is preferred for several reasons. Acetaldehyde has relatively low toxicity and is inexpensive. Also, acetaldehyde has a boiling point (about 21° C.) near room temperature so that heating is not required to readily form acetaldehyde vapors from liquid acetaldehyde in the reservoir 32. Another desirable aspect of acetaldehyde is that the derivatives formed by the reaction of acetaldehyde vapors with hydrazine compounds are volatile and therefore may readily be swept from the reaction chamber 34 into downstream portions of the analyzer for further processing.

If a ketone is used in the reservoir 32 instead of or in addition to an aldehyde, acetone is currently the ketone of choice. Like acetaldehyde, acetone is inexpensive and of low toxicity. However, since acetone has a boiling point (about 37° C.) somewhat higher than room temperature, its use will normally require some amount of heating of the reservoir 32 or the use of a carrier gas to sweep fumes of acetone out of the reservoir 32 into the sample line 36.

Aldehydes other than acetaldehyde, and ketones other than acetone, may be utilized to derivatize the hydrazine compounds. For example, formaldehyde has been used in detection of UDMH according to the detection method described herein. However, many of the aldehydes and ketones are less suitable than acetaldehyde and acetone because of their high cost, toxicity, undesirable odors, and/or high boiling points. Moreover, the higher molecular weight, higher boiling point aldehydes and ketones may produce hydrazine derivatives of insufficient volatility to readily pass from the reaction chamber 34 into the pyrolyzer.

Figure 6:
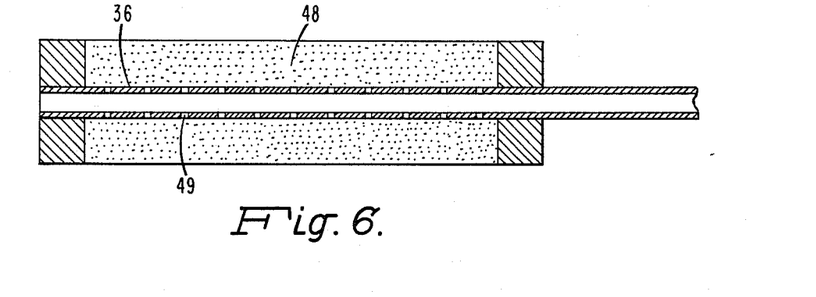
FIG. 6 shows a portion of a sample line containing an annular plug for supplying aldehyde or ketone vapors to a sample line to derivatize hydrazine compounds in a gaseous sample.

As an alternative to the reservoir 32 the sample line 36 may contain or be connected to a solid source of an aldehyde or ketone. For example, in FIG. 6 there is shown an annular plug 48 of a material such as trioxane or paraformaldehyde surrounding a portion of the sample line 36. Holes 49 are provided in the sample line 36 so that aldehyde or ketone vapors from the plug 48 flow into the line 36, coating its walls and mixing with gaseous samples drawn through the line. If the solid aldehyde or ketone source has a low vapor pressure it may be heated or a mineral acid such as sulfuric acid may be added to facilitate the evolution of aldehyde or ketone vapors.

A reaction chamber 34 is connected to the outlet end 39 of the sample line 36 to receive a mixture of sample gas and aldehyde (or ketone) vapors and permit therein the reaction of hydrazine compounds and aldehyde vapors to form hydrazine derivatives. A suitable reaction chamber 34 is a Teflon tube having an inner diameter of about ⅜ inch and a length of about 3 inches and containing a surface for aiding the derivatization reaction. One preferred surface is that provided by several stainless steel screens arranged normal to the direction of flow—e.g., a sandwich-like arrangement of six 100-mesh stainless steel screens has been found to work well. An alternative surface is that formed by ceramic fibers such as Fiberfrax material available from the Carborundum Company of Niagara Falls, New York. The stainless steel screens, in addition to providing a surface which assists in forming hydrazones and azines from hydrazine compounds and which readily releases the hydrazones and azines, also may serve as a flame arrestor. The latter may be required if the hydrazine analyzer is used in applications such as missile silos.

From the converter 30 samples are fed through a sample conduit 50 to a pyrolyzer 54. A flow restrictor 56 such as a capillary tube may be included in the conduit 50 to control the sample flow rate. The restrictor 56 permits low pressures to be maintained in the NO detector 60 and the pyrolyzer 54 (e.g., a vacuum of 25 inches of water in the NO detector 60) yet allows flow velocities through the reaction chamber 34 to remain sufficiently low that the aldehyde reaction with hydrazine compounds proceeds to completion at essentially ambient pressure and temperature.

The pyrolyzer 54 functions to produce nitric oxide (NO) from the hydrazine derivatives present in the effluent of the sample converter 30. Preferably the pyrolyzer is a temperature-controlled tube operable at temperatures greater than or equal to 600° C. (preferably at a temperature in the range of about 600° to 1000° C.) and contains a nickel surface. For example, the pyrolyzer 54 may comprise a quartz or ceramic tube of 4–5 mm. inner diameter containing a coiled nickel-containing wire 58. A tube fabricated of a nickel alloy may also be used. Temperature control for the pyrolyzer 54 is provided by an electrically-heatable wire such as a Nichrome wire or by a heater external to the pyrolyzer tube.

A source of oxygen in the pyrolyzer 54 is also required to produce NO from the combined nitrogen in the hydrazine derivatives. Oxygen present in the sample is normally a source sufficient for oxidation of the azines or hydrazones to NO. However, if required, oxygen may be separately supplied to the pyrolyzer 54. Also, oxygen in the nickel oxides formed on the nickel-containing wire or tube of the pyrolyzer 54 may temporarily sustain production of NO from hydrazine derivatives in samples without an additional source of oxygen.

Effluent from the pyrolyzer 54, including NO produced from hydrazine derivatives, is directed through an NO detector 60 and exhaust gases exit from the NO detector by an outlet 62. A preferred NO detector is a chemiluminescent analyzer utilizing the well-known reaction of NO with ozone ($O_3$) to produce "excited" nitrogen dioxide ($NO_2^*$). The $NO_2^*$ rapidly decays to "ground-state" nitrogen dioxide ($NO_2$), emitting near infrared radiation which may be detected by a photomultiplier tube which is included in either the NO detector 60 or forms part of the processor/controller 44 connected to the NO detector by a line 64. Suitable chemiluminescent NO analyzers may be obtained from several sources, including Thermo Electron Corporation of Waltham, Mass., which manufactures chemiluminescent $NO-NO_X$ detectors as its Model 10- and Model 14-series $NO-NO_X$ analyzers. Thermo Electron also manufactures and sells instruments designated as TEA ® Analyzers which include a pyrolyzer, a chemiluminescent NO detector, and a photo-multiplier tube and associated electronics. Such TEA Analyzers may readily be combined with a sample converter as described above and used in the practice of the present invention.

The processor/controller 44 may contain, in addition to a photomultiplier tube and associated electronics, means for controlling the valve 43 which regulates the flow of aldehyde or ketone from the reservoir 32 to the sample line 35 of the sample converter 30, and means for subtracting signals produced by the photomultiplier tube. It may, for example, be desirable to operate the hydrazine analyzer of the invention in two modes and to subtract signals in order to distinguish the hydrazine compounds from other nitrogen-containing compounds which are present in gas samples and produce NO when heated. In one mode of operation the processor/controller 44 sets the valve 43 in an open position to allow aldehyde vapor flow to the sample line 36 and generates a first signal indicative of the content of hydrazine compounds plus other nitrogen-containing compounds of a sample. In a second mode with the pyrolyzer 54 preferably operating at the same temperature, the processor/controller 44 closes the valve 43 and generates a second signal indicative of nitrogen-containing compounds not including any hydrazine or MMH present in the gas sample. Subtraction of the second signal from the first signal provides a direct indication of the presence and amount of hydrazine compounds contained within the gaseous sample.

It should be noted that the net signal obtained as a result of the above-described subtraction will indicate essentially all of the hydrazine and MMH present in the sample but only substantially one-half of total UDMH content. This is so because while substantially all of the UDMH is detected in the first mode of operation of the analyzer, one-half of the UDMH is also detected in the second mode (i.e., UDMH pyrolyzes to form some NO even without conversion of the UDMH to an aldehyde derivative). Thus the net signal is indicative of the total hydrazine compound content for samples which contain no UDMH, but less than this (by one-half the UDMH) for samples containing UDMH.

Figure 4:
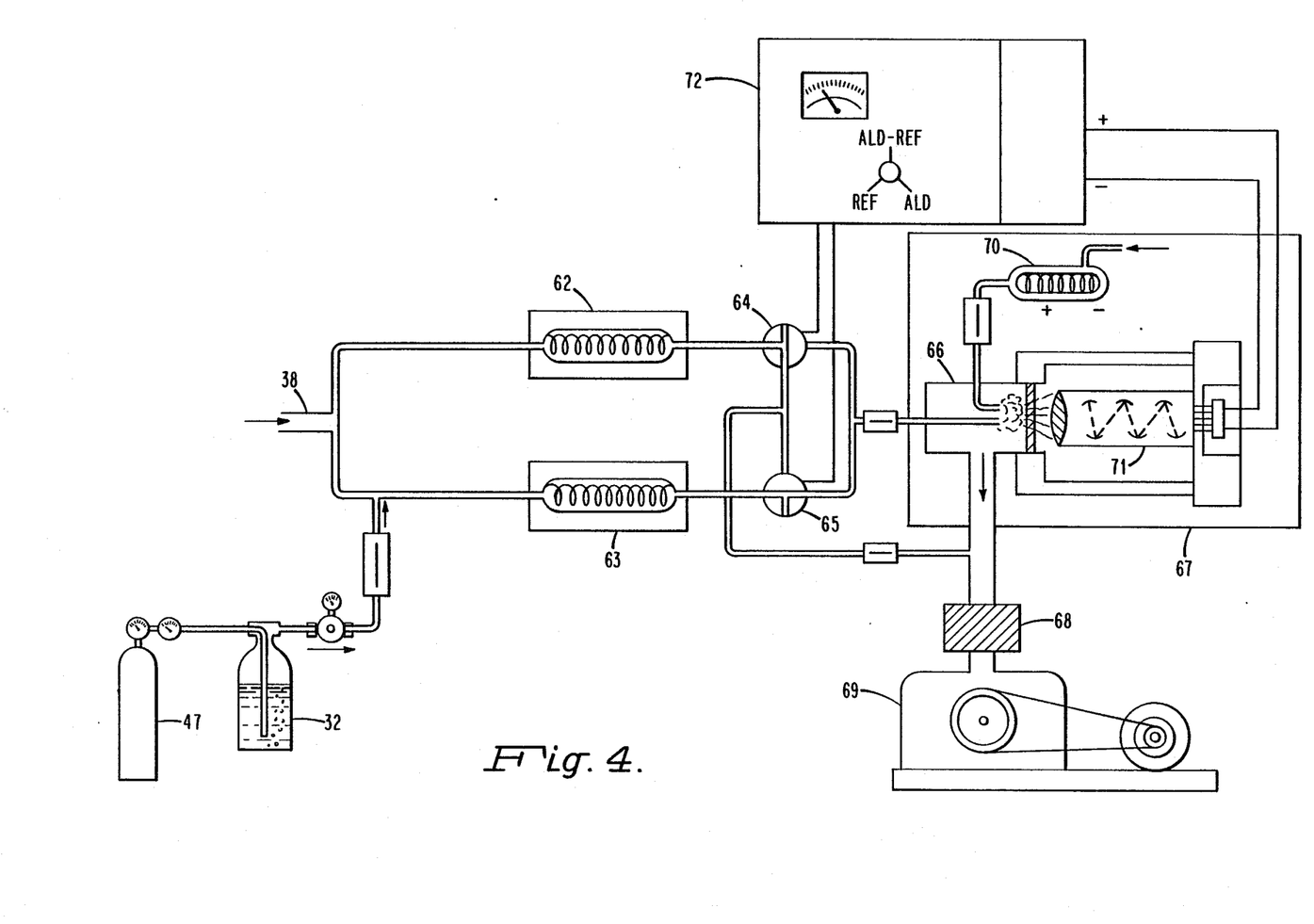
FIG. 4 is a schematic diagram of a preferred hydrazine analyzer according to the invention.

Dual mode operation may also be provided by use of the hydrazine compound detector shown in FIG. 4, which includes a reference channel having a pyrolyzer 62 in parallel with an aldehyde (or ketone) channel having a pyrolyzer 63. (Reference numerals 32, 38, and 47 in FIG. 4 are used to designate the same elements as those bearing these numerals in FIGS. 2 and 3.) The oxidation products of the pyrolyzers 62 and 63 for various compound species are indicated in Table 1, and the difference in NO resulting from subtracting reference channel signals from aldehyde channel signals illustrates the specificity of the hydrazine compound detector of the invention for hydrazine and monomethylhydrazine.

In the two above-mentioned channels, valves 64 and 65 downstream of the pyrolyzers permit flow to be directed to a reaction chamber 66 of a chemiluminescent NO detector 67 or to bypass the reaction chamber 66 and pass through an ozone remover 68 and a vacuum pump 69. In the reaction chamber 66, NO in the gas flow received from the pyrolyzers 62 and 63 reacts with ozone supplied by an ozone generator 70, and the resulting infrared emission is detected by a photomultiplier tube 71. Signals from the photomultiplier tube 71 are transmitted to a multiprocessor/display unit 72 which subtracts or combines signals from the reference and aldehyde channels as desired.

In many applications, as in monitoring silos containing missiles whose fuels may include just one of the three hydrazine compounds whose detection is discussed herein, the particular compound to be detected is known and the net signal may be used to determine, essentially in real-time, whether the allowable level of that hydrazine compound has been exceeded. In other situations the presence and amount of specific hydrazine compounds may be determined by the addition to the above-described hydrazine analyzer of a gas chromatograph.

TABLE 1

NITROGEN OXIDE (NO) FORMATION FROM AIRBORNE PRECURSORS

| COMPOUND SPECIES | OXIDATION PRODUCT | | |
|---|---|---|---|
| | REFERENCE CHANNEL (1) | ALDEHYDE CHANNEL (2) | DIFFERENCE IN NO (2) − (1) |
| $NO + O_2$ | NO | NO | — |
| $NO_2 + O_2$ | NO | NO | — |
| $N_2O + O_2$ | NO | NO | — |
| $N_2 + O_2$ | $N_2$ | $N_2$ | — |
| $NH_3 + O_2$ | $N_2$ | $N_2$ | — |
| AMINES + $O_2$ | NO | NO | — |
| NITRO COMPOUNDS + $O_2$ | NO | NO | — |
| CYANO COMPOUNDS + $O_2$ | NO | NO | — |
| HYDRAZINE + $O_2$ | $N_2$ | 2 NO | 2 NO |
| MMH + $O_2$ | $N_2$ | 2 NO | 2 NO |

TABLE 1-continued

| | NITROGEN OXIDE (NO) FORMATION FROM AIRBORNE PRECURSORS | | |
|---|---|---|---|
| | OXIDATION PRODUCT | | |
| COMPOUND SPECIES | REFERENCE CHANNEL (1) | ALDEHYDE CHANNEL (2) | DIFFERENCE IN NO (2) − (1) |
| UDMH + $O_2$ | NO | 2 NO | NO |

Figure 5:
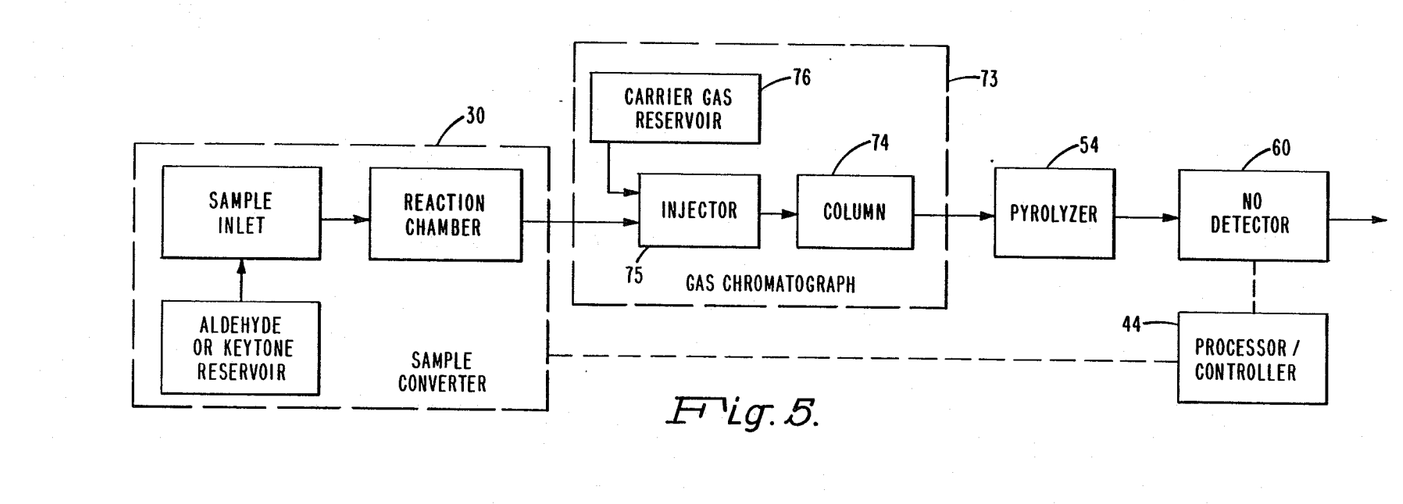
FIG. 5 is a block diagram of an alternate embodiment of the hydrazine analyzer which includes a gas chromatograph to permit identification and measurement of specific hydrazine compounds.

As illustrated in the embodiment shown in FIG. 5, a chromatograph 73 is positioned between the sample converter 30 and the pyrolyzer 54 and includes at least a separation column 74, an injector 75, and a carrier gas reservoir 76. The chromatograph 73 effects a timewise separation between the hydrazine compounds and other compounds which may yield NO when pyrolyzed and produces a separation among the hydrazine compounds themselves. This allows hydrazine, MMH, and UDMH to be individually detected (though not in real time) when two or more are present, and also allows their concentrations to be measured by the NO detector 60 and processor/controller 44.

The technique for detecting hydrazine compounds according to the invention is illustrated by the following reaction sequence which occurs to yield detectable NO when acetaldehyde is used in the derivatization of MMH:

(1) MMH+acetaldehyde→acetaldehyde hydrazone
(2) acetaldehyde hydrazone+oxygen→nitric oxide+water+carbon oxides The relevant chemical reactions for this sequence are:

Similar reactions occur when acetaldehyde is used to derivatize UDMH and when acetaldehyde is used to derivatize hydrazine except that in the latter reaction one mole of acetaldehyde azine is formed for each two moles of acetaldehyde, the azine formed having the formula A summary of the derivatizing and oxidation reactions (with acetaldehyde used as derivatizing agent) is given in Table 2. The H+ ions indicated in the derivatizing reactions are supplied by the acid formed from the aldehyde or ketone or added to the sample converter.

TABLE 2
HYDRAZINE DERIVATIZING AND OXIDATION REACTIONS

TABLE 2-continued
HYDRAZINE DERIVATIZING AND OXIDATION REACTIONS

An analyzer similar to that shown in FIGS. 1-3 has been successfully used to monitor MMH at levels ranging in concentration from 0.5 ppm to 40 ppm for a period of up to two weeks. In the test apparatus, controlled amounts of MMH were generated using a diffusion tube fitted to a reservoir containing liquid MMH and using a flow of nitrogen gas of about 20 cc/min. to sweep vapors of MMH into a sample line. Air at a flow rate of about 600 cc/min. was directed to a separate inlet of the sample line, and acetaldehyde vapors were supplied to a third inlet just ahead of a reaction chamber. The flow of acetaldehyde vapors was produced by using about 5 cc/min. of nitrogen as a carrier gas to sweep vapors of acetaldehyde leaked by a diffusion tube fitted to a reservoir containing reagent grade acetaldehyde of boiling point 21°-24° C. A 3-inch long, ⅜-inch I.D. Teflon tube at room temperature was employed as a reaction chamber, and the tube contained a sandwich-like array of six 100-mesh stainless steel screens. The reaction chamber was connected through a capillary tube having an I.D. of about 0.015 inches to a quartz pyrolyzer tube of 4-5 mm I.D. and containing a nickel alloy wire (Nickel 201). The pyrolyzer tube was surrounded by a heater operable to maintain temperatures of about 850° C. within the tube, and the pyrolyzer tube in turn was connected to a chemiluminescent NO-detector.

Figure 7:
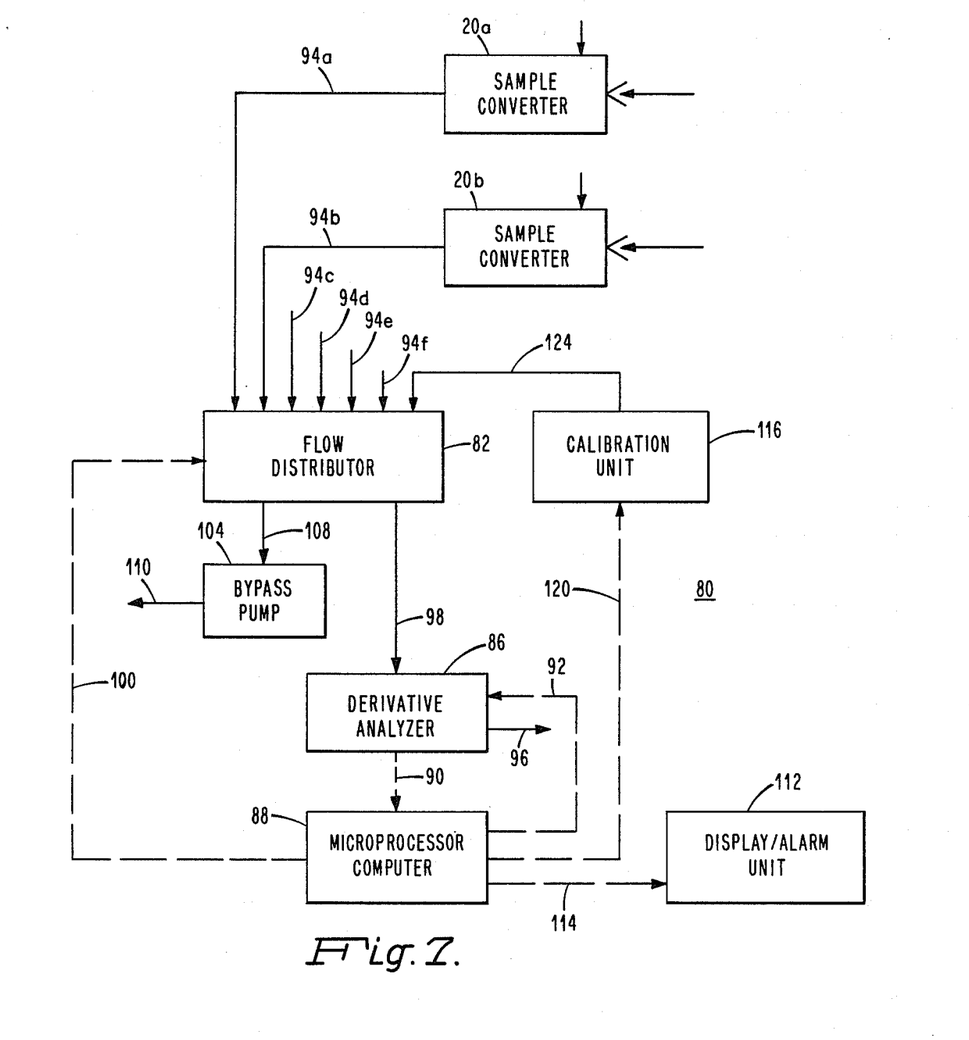
FIG. 7 is a block diagram of a hydrazine compound detection system according to an embodiment of the invention including a plurality of sample converters for forming derivatives from hydrazine compounds near multiple sample points and a derivative analyzer connected to the converters by sample lines.

The hydrazine compound detector of the invention may acquire and analyze samples essentially at a single location as in the embodiments shown in FIGS. 1-5. Alternatively, the detector may be included in a detection system as illustrated in FIG. 7 wherein sampling is performed at two or more locations and samples are analyzed at a location some distance away. The system 80 can, for example, be employed as a propellant vapor detection system for continuously sampling the atmosphere in a missile silo to monitor for leaks of fuel containing UDMH.

The detection system 80 illustrated in FIG. 7 comprises a plurality of sample converters such as the sample converters 20a and 20b connected through a flow distributor 82 to a single derivative analyzer 86 (which may include a pyrolyzer and NO detector as illustrated in FIGS. 1-5). A microprocessor-based computer 88 is electrically connected to the derivative analyzer 86 to receive output signals therefrom along a line 90 and to transmit appropriate control signals to the derivative analyzer 86 along a line 92.

The sample converters 20a, 20b, and others sch as 20c-20f not shown in the interest of clarity are each similmar to the sample converters described with reference to FIGS. 1-5. Each converter is connected by a sample line such as the lines 94a, 94b, 94c, 94d, 94e and 94f to the flow distributor 82. The flow distributor 82 includes appropriate manifolding and valving such that flow from any one of the sample converters such as the converter 20a or 20b may be directed along a common sample line 98 to the derivative analyzer 86 for analysis of its hydrazine compound content, then discharged through an outlet 96. Control of the flow distributor 82 is maintained by means of the microprocessor computer 88 which is operable to provide electrical signals to the distributor 82 along a line 100. These signals may, for example, establish a desired sampling sequence wherein each converter periodically directs flow to the derivative analyzer 86.

A bypass pump 104 is also provided for drawing flow from each converter not currently selected for analysis and diverting this flow through a bypass line 108 for discharge through an outlet 110. The bypass arrangement permits a fresh sample to be readily available from each converter as its flow is selected for analysis.

The detection system 80 may also include a display/alarm unit 112 for receiving signals from the microprocessor computer 88 along a line 114, and a calibration unit 116 connected to the computer 88 by a line 120 and to the flow distributor 82 by a line 124.

In the detection system 80 one or more of the sample lines 94a-94f may be of considerable length (150-200 feet or more) to permit deployment of the sample converters 20a, 20b, etc. at various remote locations where sampling is desired, yet permit analysis to be performed at the central derivative analyzer 86. For such configurations an advantage of converting hydrazine compounds to the above-mentioned derivatives near the sampling points rather than near the point of analysis is that the former avoids losses due to the condensation or "sticking" of hydrazine compounds in the sample lines 94a-94f or in the line 98 due to the reaction of hydrazine compounds with other substances during transport to the derivative analyzer 86. Such losses, which could result in an increase in response time or to reduced sensitivity, are avoided by converting the samples to hydrazones or azines near the remote sampling points because these derivatives, unlike hydrazine, UDMH, and MMH which tend to react with moisture and coat tubing walls, are stable and nonpolar and may readily be transported for considerable distances.

Figure 8:
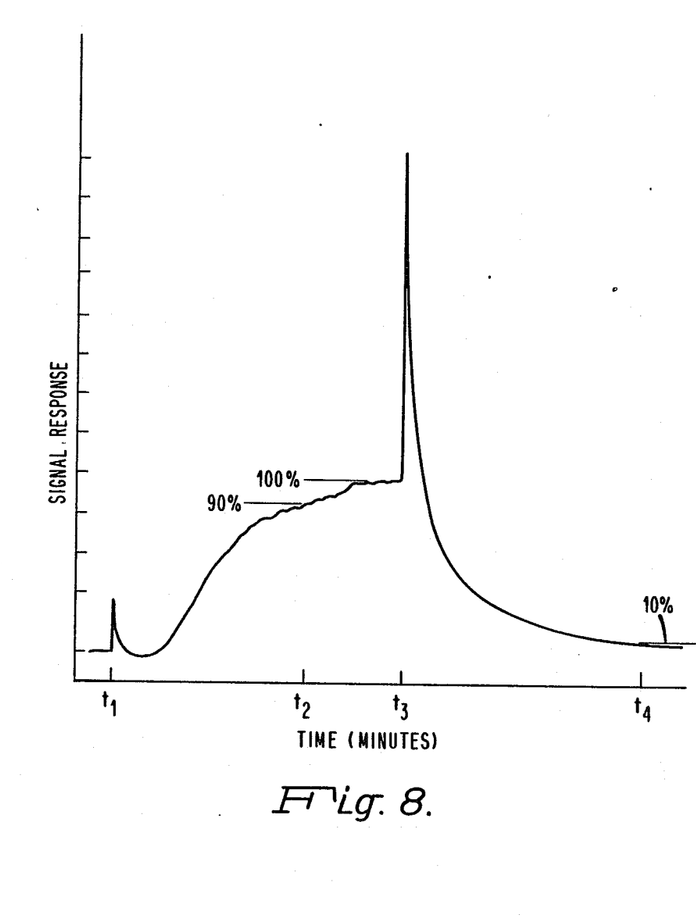
FIGS. 8 and 9 are timewise plots comparing the signal response of a hydrazine detector measuring an unconverted hydrazine (FIG. 8) with its response when measuring a hydrazine derivative formed in accordance with the invention (FIG. 9).
Figure 9:
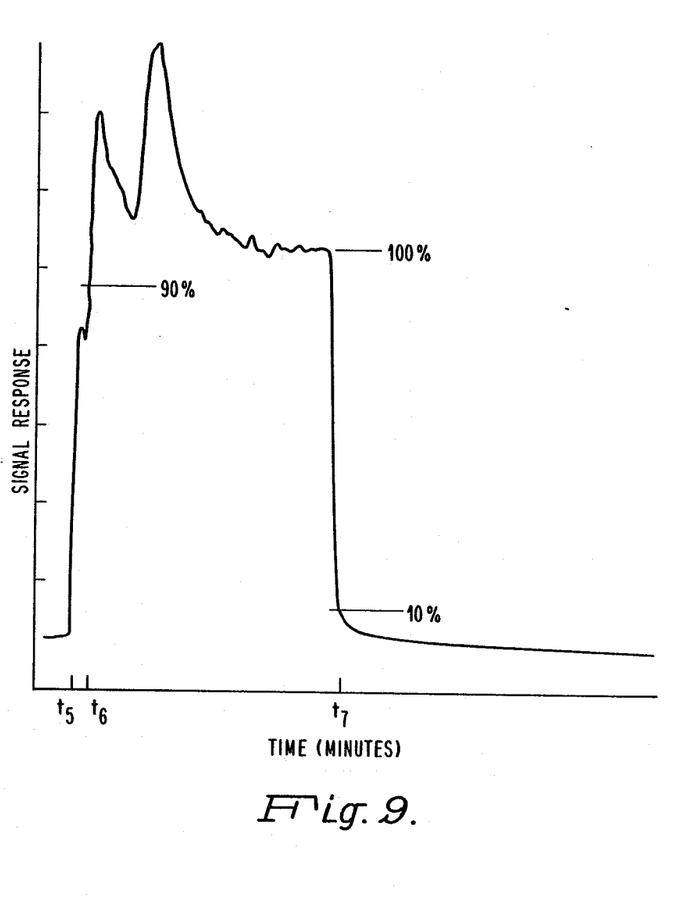

FIGS. 8 and 9 illustrate the effects of derivatization of hydrazine compounds on sample transport through an instrument having internal Teflon lines, valves, and other surfaces on which samples may adhere or stick. In FIG. 8 a timewise plot is shown of the response of the reference channel of a multi-channel hydrazine detector of the type illustrated in FIG. 4 whose input was switched at time $t_1$, from a flow of dry air at room temperature to a sample flow of UDMH plus air at a relative humidity of 80%. Approximately three minutes were required for 90 percent signal response to be attained (at time $t_2$), indicating that UDMH in the sample "stuck" on surfaces in the instrument. After full response was achieved, flow through the instrument was again switched to dry air at time $t_3$. A large spike was immediately produced in the signal, likely due to desorption of UDMH from instrument surfaces by dry room air. Signal response then slowly decayed, with over three minutes being required for 90% loss (at time $t_4$). In contrast, FIG. 9 illustrates a rapid rise in signal response achieved with the same instrument when input flow was switched at time $t_5$ from dry air to a flow of UDMH plus air at a relative humidity of 80% plus an excess of acetaldehyde vapors, and a rapid fall when dry air was reintroduced at time $t_5$. (The two peaks following the signal rise to 100 percent response are not fully understood but are believed due to vacuum pump problems.) The time for the signal to rise to 90 percent of full response was about 15 seconds and the time for 90 percent loss after reintroduction of air was about 10 seconds. These rapid responses are strong evidence that derivatization of gaseous samples containing UDMH according to the invention prevents sticking and loss of samples due to surfaces such as are present in instruments and sample lines.

Although the invention has been shown as described as particularly useful in direct, continuous, essentially real-time monitoring of gaseous samples containing hydrazine, MMH, and UDMH, it should be evident that the hydrazine detection technique of the invention can be employed to detect hydrazine compounds in liquid samples or in gas samples which have been collected prior to analysis. For example, an air sample containing hydrazine compounds may be collected by passing the sample through a liquid such as a mixture of acetone and acetic acid. A portion of the mixture is then flash vaporized and passed to a pyrolyzer having a source of oxygen and whose outlet is connected to an NO detector. Samples of UDMH and MMH may also be collected by passing air suspected of containing hydrazine compounds through cartridges containing a granular sorbent packing such as magnesium silicate, then eluting the compounds with a liquid such as acetone. A portion of the eluent is then flash vaporized, pyrolyzed, and analyzed for NO content. In either case the hydrazine derivatives of aldehyde or ketone are formed while the hydrazine compounds are in contact with the liquid aldehyde or ketone. Also, a gas chomatograph (with an appropriate injector including a flash vaporization heater) may be connected to the inlet of the pyrolyzer if it is desired to identify specific hydrazine compounds and their concentrations.

Thus there has been disclosed a method and apparatus for continuous, real-time analysis of samples, particularly gas samples, for the presence and amount of hydrazine, monomethylhydrazine (MMH), and unsymmetrical dimethylhydrazine (UDMH). The hydrazine analyzer is sensitive to these hydrazine compounds at levels from about 1-2 parts per billion to about 200 parts per million, is reliable, and is free from known interferences.

What is claimed is:

1. A method of detecting the presence of hydrazine, monomethylhydrazine, and unsymmetrical dimethylhydrazine in a gaseous sample, essentially in real time, comprising in the order given the steps of:
   (a) contacting a gaseous sample with aldehyde or ketone vapors to convert hydrazine, monomethylhydrazine, and unsymmetrical dimethylhydrazine in said sample to hydrazine derivatives;
   (b) heating said sample in the presence of an oxidant to decompose derivatives produced in steps (a) to produce nitric oxide gas; and
   (c) determining the amount of nitric oxide gas produced in step (b), wherein any nitric oxide gas determined is indicative of the presence of hydrazine, monomethylhydrazine, and unsymmetrical dimethylhydrazine in said gaseous sample.

2. A method as in claim 1 wherein the steps are performed continuously so as to provide continuous detection of hydrazine, monomethylhydrazine, and unsymmetrical dimethylhydrazine.

3. A method as in claim 1 wherein the amount of nitric oxide gas produced in step (b) is determined by reacting any nitric oxide gas with ozone and measuring the intensity of any resultant chemiluminescent emission.

4. A method as in clam 1 wherein said aldehyde is acetaldehyde.

5. A method as in claim 1 wherein said converting step includes passing said sample through a perforated tube surrounded by a solid, readily vaporizable source of aldehyde vapors.

6. A method as in claim 1 wherein said heating step comprises heating said sample to a temperature in the range of about 600° C. to 1000° C.

7. A method as in claim 6 wherein said heating step comprises heating said sample in the presence of air and nickel.

8. A method of continuously detecting the presence of hydrazine, monomethylhydrazine, and unsymmetrical dimethylhydrazine in a gaseous sample, essentially in real time, comprising:
   (a) contacting a gaseous sample with acetaldehyde to convert hydrazine, monomethylhydrazine, and unsymmetrical dimethylhydrazine in said sample to hydrazine derivatives;
   (b) heating said sample in the presence of air to decompose hydrazine derivatives produced in step (a) to produce nitric oxide gas; and
   (c) determining the amount of nitric oxide gas produced in step (b) wherein any nitric oxide gas determined is indicative of the presence of hydrazine, monomethylhydrazine, and unsymmetrical dimethylhydrazine in said gaseous sample.

9. A method of determining the total amount of hydrazine and monomethylhydrazine, and about one-half the amount of unsymmetrical dimethylhydrazine in a gaseous sample comprising the steps of:
   (a) converting hydrazine, monomethylhydrazine, and unsymmetrical dimethylhydrazine in a first portion of a gaseous sample to hydrazine derivatives by contacting said first portion with an aldehyde, a ketone, or a mixture thereof;
   (b) heating said first portion of said gaseous sample to a first predetermined temperature in the presence of an oxidant to decompose hydrazine derivatives produced in step (a) to produce nitric oxide gas;
   (c) determining the amount of nitric oxide gas produced in step (b);
   (d) heating a second portion of said gaseous sample to a second predetermined temperature in the presence of an oxidant;
   (e) determining the amount of nitric oxide gas produced in step (d); and
   (f) subtracting the amount of nitric oxide gas determined in step (e) from the amount of nitric oxide gas determined in step (c); the amount of nitric oxide gas resulting from said subtraction being indicative of the sum of the amounts of hydrazine and monomethylhydrazine and about one-half the amount of unsymmetrical demethylhydrazine present in said gaseous sample.

10. A method as in claim 9 wherein the converting step comprises contacting said first portion of the sample with vapors of acetaldehyde.

* * * * *